United States Patent [19]

Chandler

[11] Patent Number: 4,585,623
[45] Date of Patent: Apr. 29, 1986

[54] DEVICE FOR PERFORMING QUANTITATIVE CHEMICAL AND IMMUNOCHEMICAL ASSAYS

[75] Inventor: Howard M. Chandler, Orton, Canada
[73] Assignee: Allelix Inc., Mississauga, Canada
[21] Appl. No.: 722,178
[22] Filed: Apr. 10, 1985

Related U.S. Application Data

[63] Continuation of Ser. No. 584,007, Feb. 27, 1984, abandoned.

[51] Int. Cl.⁴ .................... G01N 1/00; G01N 33/53
[52] U.S. Cl. .................... 422/57; 137/512.4; 137/859; 137/877; 422/58; 422/61; 422/68; 422/100; 422/102; 422/103; 435/291; 435/296; 435/808; 436/809; 436/810
[58] Field of Search .................... 422/55, 57, 58, 61, 422/68, 85, 86, 88, 100, 102, 103; 436/809, 810, 807; 435/287, 288, 291, 296, 808; 222/135, 494; 141/9.35; 137/512.4, 566, 567, 859, 877

[56] References Cited

U.S. PATENT DOCUMENTS

| | | | |
|---|---|---|---|
| Re. 31,006 | 8/1982 | Schuurs et al. | |
| 3,370,175 | 2/1968 | Jordan et al. | 435/291 X |
| 3,475,128 | 10/1969 | Thiers | 422/103 X |
| 4,237,096 | 12/1980 | Popoff et al. | 141/35 X |
| 4,324,758 | 4/1982 | Eisentraut et al. | 422/61 |
| 4,458,020 | 7/1984 | Bohn et al. | 435/296 |

FOREIGN PATENT DOCUMENTS

| | | |
|---|---|---|
| 7712933 | 11/1978 | France . |
| WO82/02211 | 7/1982 | PCT Int'l Appl. . |
| WO83/01119 | 3/1983 | PCT Int'l Appl. . |

OTHER PUBLICATIONS

UCG-Beta Stat- 1980 Horner.

Primary Examiner—Barry S. Richman
Assistant Examiner—Robert J. Hill, Jr.
Attorney, Agent, or Firm—Ridout & Maybee

[57] ABSTRACT

The invention provides a device for performing chemical or immunochemical assays quickly and on site. The device comprises a plastic molded body which may be miniaturized. The device is provided with a plurality of tubes for containing assay reagents, a small bore tube in which the assay is carried out, a sample tube, and conduit and valve means from the various tubes to the assay tube. The device is insertable into a programmable apparatus which controls the flows of the various reagents through the assay tube by means of plungers acting on pistons located in each reagent tube.

14 Claims, 7 Drawing Figures

DEVICE FOR PERFORMING QUANTITATIVE CHEMICAL AND IMMUNOCHEMICAL ASSAYS

This application is a continuation of application Ser. No. 584,007, filed Feb. 27, 1984, now abandoned.

The present invention relates to a device for rapidly performing quantitative or qualitative chemical or immunochemical assays which preferably makes use of available miniaturization and computer technologies to provide an inexpensive and automated assay system.

The preferred device is in the form of a plastic chip insertable into a programmable operating and analyzing apparatus. The device allows for the performance of assays on the spot thereby rapidly providing data, for example, to a physician for diagnostic purposes.

Presently, most assays in the form of medical testing or otherwise, are performed in central laboratories to which test samples are sent. Such assays generally are conducted in accordance with a batch system whereby relatively large volumes of special reagents and frequently complex and expensive apparatus are used. Thus, the cost of obtaining assay data is generally increasing while the time required to obtain that data is not decreasing.

As present day medical care in particular is relying increasingly on analytical data from patient testing to arrive at a proper diagnosis and course of treatment, it is becoming ever more important to be able to provide reliable test data on the spot.

In other circumstances where assay data is needed, such as agricultural testing for pesticide residues, the need for quick and reliable results cannot be addressed by conventional centralized methods. Therefore, by providing a small and simple device enabling the performance of on side assays, the present device represents a significant advance in the art.

The operating and analyzing apparatus associated with the present device comprises a programmable minicomputer of a size to be conveniently portable. The analyzing apparatus may be capable of performing several assays simultaneously. This apparatus represents a fixed cost to the user, and it is anticipated that the extremely low cost of supplying the device of the invention will enable the user to perform a quick assay at a fraction of the cost of the same test performed presently at a central testing laboratory.

Accordingly, the present invention provides a device for performing quantitative or qualitative chemical and immunochemical assays comprising a body having a planar front surface, and the body defining therein a test sample tube, a plurality of reagent tubes, and an assay tube. Each of said tubes has an opening at the front surface of the body, and the sample and reagent tubes also have an opening at the rear of the body. The assay tube has a discharge opening. The front surface of the body has one or more grooves therein for connecting the openings of the sample and reagent tubes to the opening of the assay tube. A thin sheet of resiliently flexible material is affixed to the front surface of the body and coacts with the one or more grooves therein to provide a conduit system through which the fluid contents of the sample and reagent tubes may flow. Valve means which may be formed integrally with the sheet affixed to the front surface of the body coact with the opening for the sample tube and at least some of the openings for the reagent tubes for directing the flow of fluid from said tubes therebetween and through the assay tube in the manner and sequence required to perform the assay. Pistons are slidably disposed in the sample tube and reagent tubes for forcing fluid therefrom into the conduit.

BRIEF DESCRIPTION OF THE DRAWINGS

A description of a preferred embodiment of the invention follows with reference being made to the drawings in which.

Figure 7:
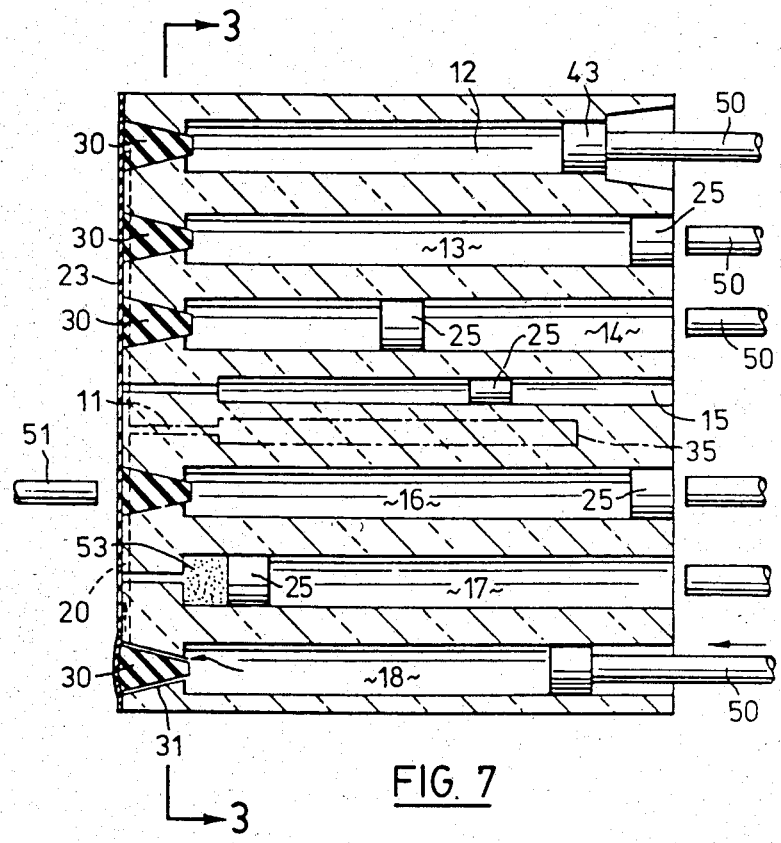
FIG. 7 is a sectional view of the device taken along line 7—7 of FIG. 1.

The preferred device of the invention comprises a body 10 preferably molded from a suitable plastic, which may be polystyrene or polyvinylchloride into which is formed an assay tube 11 (FIG. 7) and a plurality of reagent tubes 12-18. The number and configurations of the reagent tubes will vary depending on the requirements of the particular assay being performed, and it should be understood that the configuration hereinafter described pertains to a device for conducting a specific assay and for illustrating the general principles of the invention.

The device 10 as shown in the drawings is designed to perform an assay for the presence of human chorionic gonadotropin (HCG) in urine or blood. This is a common assay for determining pregnancy. The immunological assay for HCG makes use of the antigenic nature of HCG by detecting the capture of HCG by the antibody specific therefor, i.e. anti-HCG. In the present device 10, the inner surface of the assay tube 11 is provided with a coating of anti-HCG bonded thereto. A sample of blood or urine to be assayed is passed through the assay tube 11 and if HCG is present, a portion of it will bond to or be captured by the anti-HCG. To determine if any HCG has bonded to the anti-HCG in the tube 11, a solution containing anti-HCG to which has been bonded an enzyme (anti-HCG/enzyme conjugate) is passed through the assay tube 11 and if HCG has been captured therein, the anti-body portion of the conjugate will bind to a portion of the HCG present. Finally a substrate for the enzyme portion of the conjugate is introduced into the assay tube 11, and if there is enzyme present, the substrate will be metabolized by the enzyme and the metabolic products can be detected usually by colorimetric means.

The structure of the present device 10 is designed to provide reservoirs for the test sample and reagents needed for the assay as well as valve and conduit means for directing the sequential flow of fluids through the assay tube 11. The tube 12 (FIGS. 1 and 7) is for the test sample, while the remaining tubes 13-18 are for various reagents required to carry out the assay.

Figure 2:
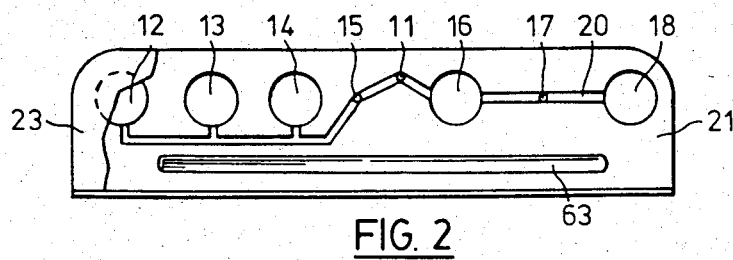
FIG. 2 is a sectional view taken along line 2—2 in FIG. 1.

The flow of liquids from the tubes 12-18 through the assay tube 11 is accomplished by means of a channel 20 formed in the front face 21 of the device 10 (see FIG. 2).

The channel 20 forms a conduit for the flow of liquids by the addition of a thin resiliently flexible sheet 23 affixed to the front face 21. The sheet 23 is preferably made of a plastic material. The liquids are forced from the tubes 12–18 by means of piston 43 (tube 12) and pistons 25 (tubes 13–18) inserted therein from the rear ends thereof at the time the tubes 12–18 are filled.

Valve means for the flow of liquids from the various tubes 12–18, along the channel 20 and then through the assay tube 11, is provided by frustoconically shaped plugs 30 which may be formed integrally with the plastic sheet 23 and which fit into frustoconical outlets 31 at the front ends of the appropriate tubes (in the device shown, tubes 12, 13, 14, 16 and 18). These plugs 30 seal the outlets 31, but are easily displaced by pressure being applied to the piston 25 in the tube to allow liquid to flow from the tube into the channel 20.

For the disposal of liquids which have passed through the assay tube 11, the device 10 is provided with a waste reservoir 35 defined on five sides by the body of the device 10 itself and on the sixth side comprising the bottom thereof, the reservoir is provided with a flexible plastic membrane 36. The membrane 36 can be attached to the bottom of the device 10 so as to form a concave wall thereby reducing the volume of the unused reservoir 35. Upon the entry of liquids into the reservoir 35, the membrane 36 can expand to accommodate the additional volume. By this arrangement there is no need to provide a vent for the reservoir 35.

The present device 10 is designed to take advantage of the benefits derivable from miniaturizing the assay system. These benefits include lower cost of reagents needed to perform the assay and easy portability of assay system. The dimensions of the device shown for conducting a pregnancy test may be as little as about 20 mm×20 mm×4 mm, and in a preferred embodiment the same and reagent tubes each define a volume of about 50 $\mu$l. The sample tube 12 for a device of this size is provided with 50 $\mu$l of blood or urine by means of a microsyringe 40 insertable into the rear end 41 of the tube 12. The syringe 40 receives the test sample by capillary action. The syringe 40 is provided with a notch or slot 42 in the inner wall thereof to cause the take up of sample by capillary action to stop at the desired volume, e.g. 50 $\mu$l. The syringe 40 is provided with a piston 43 and a plunger 44 not attached to the piston 43. The bore diameter of the syringe 40 is the same as that of the sample tube 12. The outlet end 46 of the syringe 40 fits into the rear end 41 of the tube 12 and the test sample along with the piston 43 are inserted into the tube 12 by means of the plunger 44 which is long enough to just insert the piston 43 into the end of the tube 12. The air displaced from the tube 12 vents past the conical plug 30 in the outlet 31 of the assay tube 11 to the waste reservoir 35.

The tube 13 is provided with 50 $\mu$l of a first wash solution, tube 14 contains 20 $\mu$l of the antibody/enzyme conjugate solution, and the small tube 15 contains an antibody coating solution for the wall of the assay tube 11. The tube 16 has 50 $\mu$l of a second wash solution, tube 17 contains a small amount of powdered enzyme substrate 53, and the final tube 18 contains a solution into which the substrate in tube 17 will be dissolved. This latter solution also contains an indicator for detecting the presence of enzyme metabolites.

The method by which the tubes 13–18 are filled and the pistons 25 inserted is well established in the art. It should be noted that the tube 15 for the coating solution is not plugged at its outlet. Thus, upon filling of the tube 15 the piston 25 is inserted and displaced toward the outlet end of the tube 15 causing coating solution to flow into the assay tube 11 via the channel 20. This filling procedure then provides the mechanism for filling the assay tube 11 with the antibody, antigen or hapten which it is desired to become bound to the inner surface of the assay tube 11. At a subsequent time, the filling of the sample tube 12 by means of the syringe 40 will cause the air being displaced from the tube 12 to flush out any coating solution remaining in the assay tube 11.

The operation of the assay is automatically performed by inserting the device 10 having the sample in the tube 12 into a preprogrammed operating and analyzing apparatus (not shown) having pipe 50 which act as plungers for the pistons 25 and 43 to cause the various solutions to pass from the tubes 12–18 through the assay tube 11 at the rate and in the sequence desired. An additional pin 51 is provided at the front of the device 10 to interact with the plug 30 in the tube 16 for the valving purpose described below.

Upon activation of the assay program, which in this case would be for the HCG assay in blood or urine, the plunger pin 50 for the tube 12 causes the sample liquid to flow slowly through the tube 11. As mentioned, pressure from the piston 43 causes the plug 30 at the outlet 31 of the tube 12 to come unseated thereby allowing the sample liquid to flow into the channel 20 and through the assay tube 11. To ensure that the sample liquid does not flow past the entry to the assay tube 11 and possibly contaminate the reagents in tubes 16–18, the pin 51 engages the plug 30 at the outlet 31 of the tube 16 thereby positively blocking the channel 20 at that point.

The flow of sample through the assay tube 11 should proceed for approximately one minute. The reaction between the antibody attached to the tube wall and the antigen in the sample is diffusion controlled. By continuously bathing the attached antibody with a flow of sample, the reaction rate is optimized and the sensitivity of the assay thereby much increased over that possible with a standard static incubation type assay. This continuous flow technique takes advantage of the principles of affinity capture and reactant concentrations to optimize the reaction kinetics at the wall of the assay tube 11.

While the sample is flowing through the assay tube 11, and with the pin 51 engaging the plug 30 at the outlet of tube 16, the pin 50 for the tube 18 is activated to force the solution from the tube 18 into the tube 17 which contains the powdered enzyme substrate 53. For the HCG assay, the preferred enzyme label is urease and the substrate in tube 17 is therefore urea. The urea is maintained in a powdered and dry state in the tube 17 until near the time it is to be used in the assay so that the purity of the urea is ensured. Urea maintained in solution gradually hydrolyses, so use of dry urea in the device provides a much longer shelf life. The urea readily dissolves in the aqueous solution introduced into the tube 17, and the solution also contains an indicator for the degradation products of urea, i.e. $CO_2$ an $NH_3$. The liberation of $NH_3$ by the action of urease on urea causes a rise in the pH of the aqueous solution which may be detected by a pH indicator such as bromthymol blue.

When the piston 25 in the tube 12 is fully depressed, the pin 50 for the tube 13 rapidly pushes the piston 25 through the full length of the tube 13 expelling the first wash solution through the assay tube 11 and into the waste reservoir 35. The enzyme/antibody conjugate solution in the tube 14 is then slowly forced through the assay tube 11 by the pin 50 and piston 25 for the tube 14. The flow of conjugate solution should proceed for at least one minute to ensure reaction with any captured HCG at the tube wall. Once again, this continuous flow procedure provides much improved reaction kinetics at the wall of the assay tube 11 for the reasons explained above.

The pin 51 sealing the tube 16 is at this point retracted and the second wash solution in tube 16 is forced through the tube 11. This wash is followed immediately by the flow of substrate solution from the tube 17.

Figure 3:
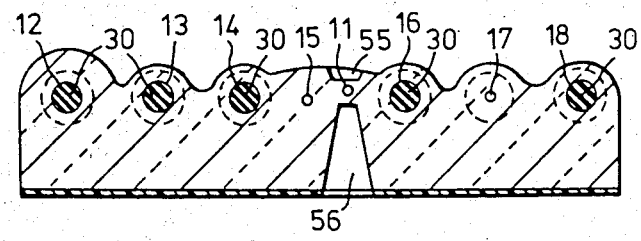
FIG. 3 is a sectional view taken along line 3—3 in FIG. 1.
Figures 4, 5, 6:
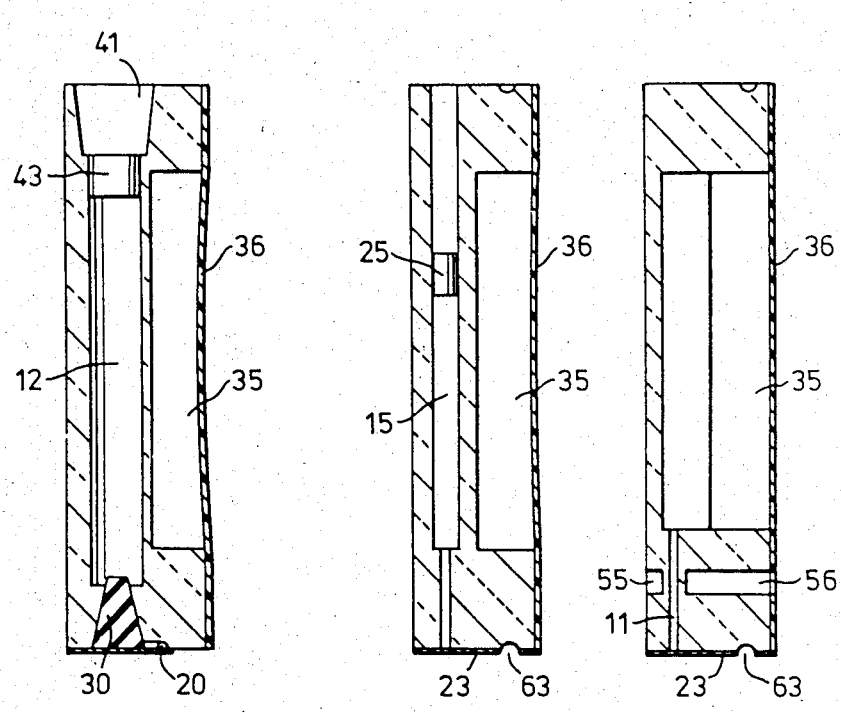
FIG. 4 is a sectional view taken through the sample tube along line 4—4 in FIG. 1.
FIG. 5 is a sectional view taken through the coating solution tube along line 5—5 in FIG. 1.
FIG. 6 is a sectional view taken through the assay tube along line 6—6 in FIG. 1.

The assay tube portion of the device 10 is provided with notches 55 and 56 above and below a portion thereof (see FIGS. 1 and 3). These notches 55 and 56 are to locate the optical heads the colorimetry instrument (not shown) which are used to monitor the change in optical density. The rate of optical density changes for the test sample is compared to that of reference standards which may be run simultaneously or stored in memory to provide a quantitative result for the assay. Measuring the rate of color development, rather than taking a single O.D. reading, should enable more accurate quantitation of results as errors caused by optical flaws or variations in the plastic used will be eliminated.

Figure 1:
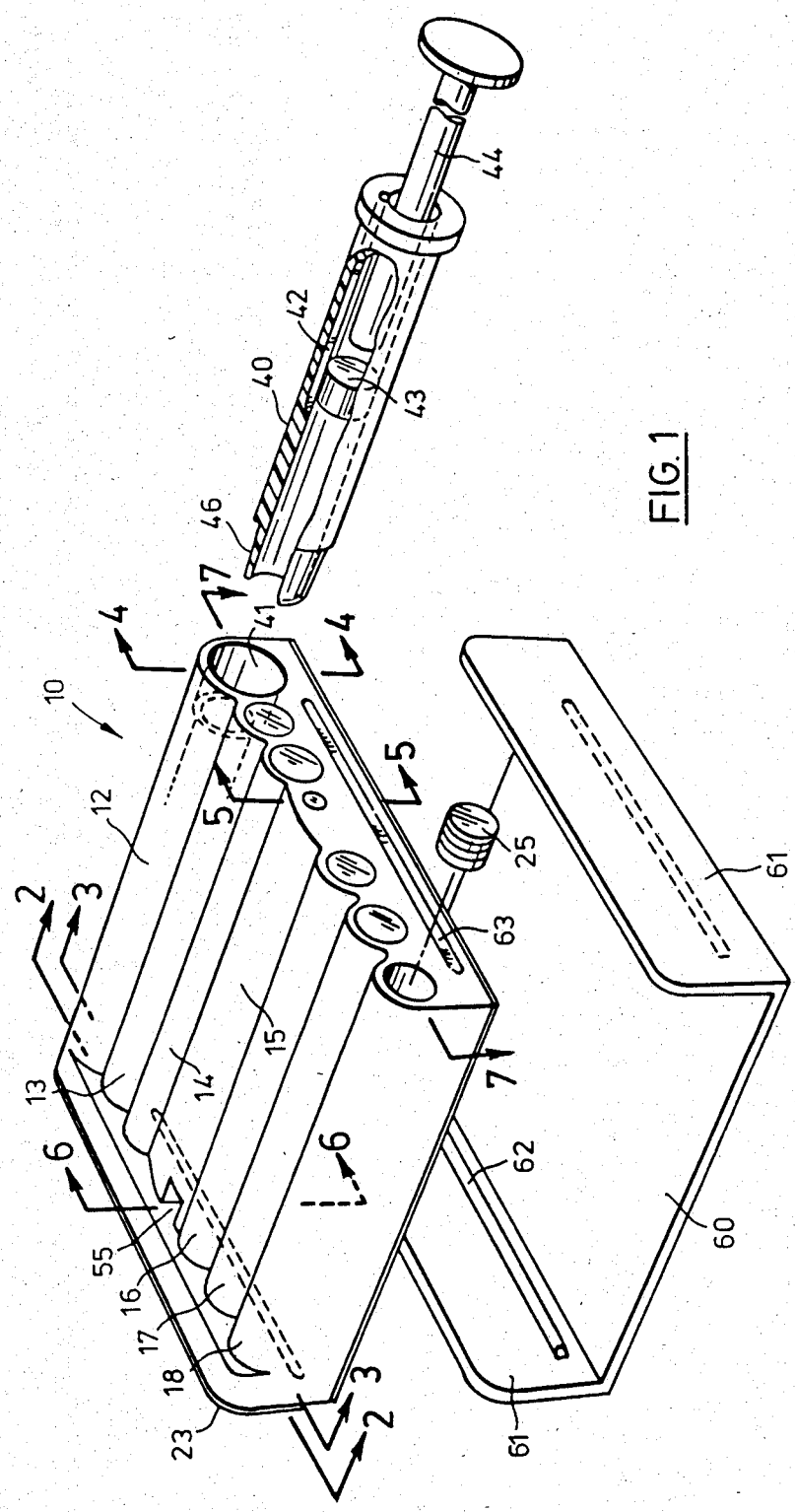
FIG. 1 is a perspective and partially exploded view of the assay device, the sample syringe and the protective clip.

For protection of the device 10 during storage and transportation, a protective clip 60 may be provided as shown in FIG. 1. The clip 60 has sides 61 which cover the front and rear surfaces of the device 10. The clip 60 is held in place about the device 10 by means of ribs 62 on the sides 61 which engage complementary grooves 63 in the body of the device 10. The clip also holds the plugs 30 and pistons 25 in place thus preventing exchange or cross-contamination of reagents.

While the preferred embodiment described relates to the performance of an assay for HCG in blood or urine, it should be understood that the principles of the invention are of general application to a large number of immunological and chemical assays which may be carried out by the present device suitably adapted for the particular purpose.

I claim:

1. A device for performing quantitative or qualitative chemical and immunochemical assays comprising:
   a body having a planar front surface and a rear surface, the body defining therein a test sample tube, a plurality of reagent tubes, and an assay tube having an inner surface, each of said tubes having an opening communicating with the front surface of the body, each of the sample and reagent tubes also having an opening communicating with the rear surface of the body and the assay tube having a discharge opening, the front surface of the body having one or more grooves therein for connecting the openings of the sample and reagent tubes that communicate with the front surface of the body to the opening of the assay tube that communicates with the front surface of the body;
   a thin sheet of resiliently flexible material being affixed to the front surface of the body coacting with the one or more grooves therein to provide a conduit system through which fluid contents of the sample and reagent tubes may flow;
   valve means coacting with the opening of the sample tube that communicates with the front surface of the body and at least some of the openings of the reagent tubes that communicate with the front surface of the body for directing flow of fluids from said tubes therebetween and through the assay tube in a manner and sequence required to perform an assay; and
   pistons slidably disposed in the sample tube and reagent tubes for forcing fluid therefrom into the conduit system.

2. A device as claimed in claim 1, wherein the valve means comprise frustoconical plugs insertable into frustoconical openings of the sample and selected reagent tubes.

3. A device as claimed in claim 1, wherein the valve means are formed integrally with the sheet affixed to the front surface of the body.

4. A device as claimed in claim 1, further comprising a protective and sealing clip for covering the front and rear surfaces of the body during storage and shipping thereof.

5. A device as claimed in claim 1, wherein the sample and reagent tubes each define a volume of about 50 $\mu$l.

6. A device as claimed in claim 1, further comprising notches in the body both above and below a portion of the assay tube, said notches providing access for detection means for measuring a parameter associated with contents of the assay tube thereby providing assay results.

7. A device as claimed in claim 1, wherein one of said plurality of reagent tubes has an opening communicating with the front surface of the body that provides direct communication with the assay tube via the conduit system, said reagent tube containing an antibody, antigen or hapten solution for coating the inner surface of the assay tube.

8. A device as claimed in claim 1, further comprising a waste reservoir defined by the body on all but one side, which one side is provided by a thin flexible membrane attached to the body, the reservoir communicating only with the discharge opening of the assay tube.

9. A device as claimed in claim 8, wherein the flexible membrane is provided on the body so as to form a concave wall for the reservoir which can expand outwardly to accommodate fluids being deposited in the reservoir.

10. A device as claimed in claim 1, wherein the assay tube is coated on its inner surface with an antibody, antigen or hapten.

11. A device as claimed in claim 10, wherein said antibody, antigen or hapten is bonded to the inner surface of the assay tube.

12. A device as claimed in claim 1, wherein the body is made of a plastic material.

13. A device as claimed in claim 12, wherein the plastic is polystyrene.

14. A device as claimed in claim 12, wherein the plastic is polyvinylchloride.

* * * * *